United States Patent [19]

Fujita et al.

[11] Patent Number: 4,935,949
[45] Date of Patent: Jun. 19, 1990

[54] GANTRY FOR COMPUTERIZED TOMOGRAPHY

[75] Inventors: Kenjiro Fujita; Masahiko Hasumi; Ryo Takahashi, all of Tokyo, Japan

[73] Assignee: Yokogawa Medical Systems, Limited, Tokyo, Japan

[21] Appl. No.: 251,223

[22] PCT Filed: Jan. 30, 1987

[86] PCT No.: PCT/JP87/00063
§ 371 Date: Jul. 22, 1988
§ 102(e) Date: Jul. 22, 1988

[87] PCT Pub. No.: WO87/04609
PCT Pub. Date: Aug. 13, 1987

[30] Foreign Application Priority Data

Jan. 31, 1986 [JP] Japan ................ 61-19856

[51] Int. Cl.$^5$ .............................. H05G 1/02
[52] U.S. Cl. ........................ 378/198; 378/4; 901/1
[58] Field of Search ............... 378/195–198; 901/1; 180/167–169

[56] References Cited

U.S. PATENT DOCUMENTS

| | | | |
|---|---|---|---|
| 2,818,510 | 12/1957 | Verse | 378/197 |
| 3,086,465 | 4/1963 | Montfort | 180/167 |
| 3,617,749 | 11/1971 | Massiot | 378/198 |
| 3,628,624 | 12/1971 | Wesener | 180/168 |
| 3,790,805 | 2/1974 | Foderaro | 378/198 |
| 3,803,417 | 4/1974 | Isok | 378/197 |
| 4,127,775 | 11/1978 | Ohlson | 378/197 |
| 4,593,239 | 6/1986 | Yamamoto | 180/167 |
| 4,716,581 | 12/1987 | Barnd | 378/198 |

FOREIGN PATENT DOCUMENTS 2806956 8/1979 Fed. Rep. of Germany ...... 378/197
0050015 9/1980 Japan.

*Primary Examiner*—Craig E. Church
*Assistant Examiner*—John C. Freeman
*Attorney, Agent, or Firm*—Moonray Kojima

[57] ABSTRACT

A gantry for computerized tomographs that can be freely moved up to or away from a patient on an operating table has been developed. It consists of a gantry main body (1) and mobile trolley section (2) that runs along a guideline formed on the floor with the gantry mounted.

8 Claims, 3 Drawing Sheets

GANTRY FOR COMPUTERIZED TOMOGRAPHY

(TECHNICAL FIELD)

This invention is related to an improved gantry for computerized tomographs. In other words, this invention is related to the gantry mounted on a trolley that can be freely moved up to or away from a patient on an operating table to facilitate the required tomography during surgery.

(BACKGROUND ART)

Because the computerized tomograph (hereinafter called the CT) requires projection data from multiple directions on the section of the subject under examination, an X-ray computerized tomographic scanner has an X-ray tube and X-ray detector installed on the gantry as integral parts, and revolves around the subject while collecting projection data at each specified angle of revolution. Projection data collected from multiple directions are processed by a computer to reconstruct sectional images. For surgery patients, a tomograph of the affected parts are taken before surgery to confirm the parts of patients to be operated on or to determine the method of surgery. Tomography is used after surgery to check the results. If tomography can be performed during an operation, the progress of the operation and proper treatment can be checked on the spot, which helps to determine whether the operation should be continued or terminated. Note that because a patient being operated on cannot be moved to where the CT scanner is installed, tomography during surgery was previously not possible.

(DISCLOSURE OF THE INVENTION)

The object of this invention is to provide a gantry for making computerized tomographs by moving the equipment up to or away from a patient on an operating table to facilitate the required tomography during surgery.

The gantry for computerized tomographs of this invention features a gantry main body (1), and a mobile trolley (2) on which the gantry is mounted, and which runs along a guide line installed on the floor.

(BRIEF DESCRIPTION OF DRAWINGS)

FIG. 2 is a plan view and FIG. 3 is a side view.

(BEST MODE FOR CARRYING OUT THE INVENTION)

Figure 1:
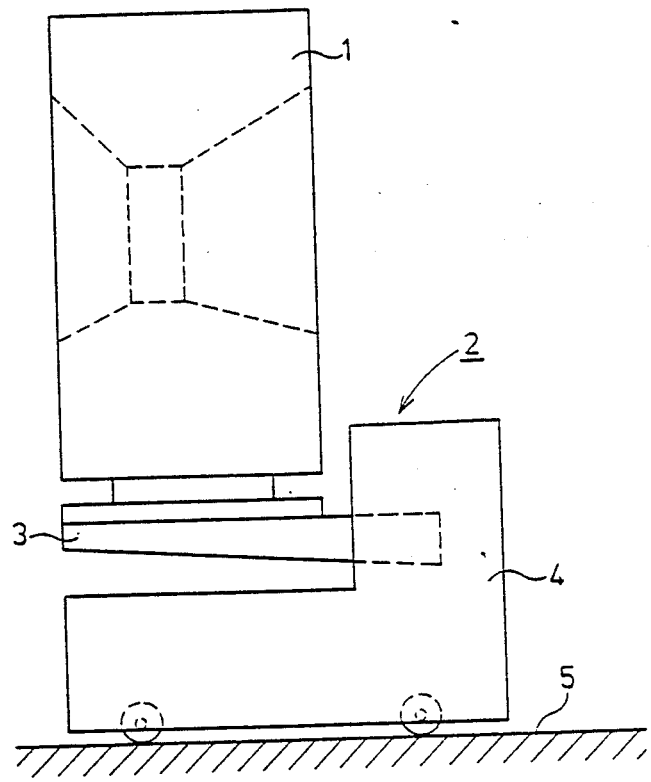
FIG. 1 is a schematic block diagram of an embodiment of this invention.

An embodiment of the invention is described by using an example and with reference to the accompanying drawings. In FIG. 1, "1" designates the gantry main body. A part of patient's body to be subjected to tomography is received in the hollow space to collect projection data on the sections. Gantry main body 1 is connected to a computer and power supply with cables not shown in the figure "2" designates a trolley consisting of roof or platform 3 and supporting base 4. Gantry main body 1 is mounted on roof 3, while the trolley moves on floor 5. Base 4 has various mechanism types as shown in FIGS. 2 and 3.

Figure 2:
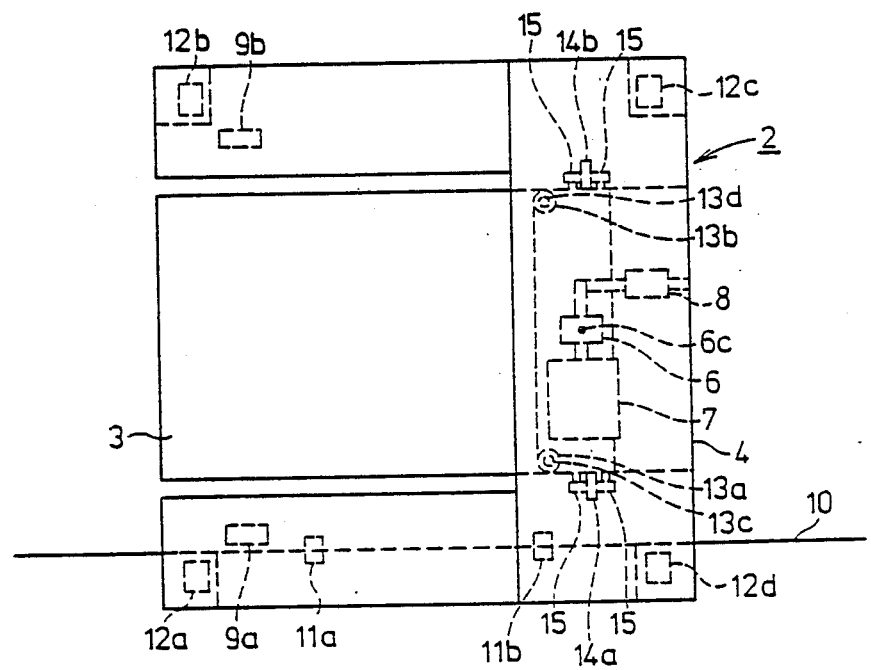
FIG. 2 and 3 are block diagrams of the trolley section, and show a part of the example of the embodiment of this invention.
Figure 3:
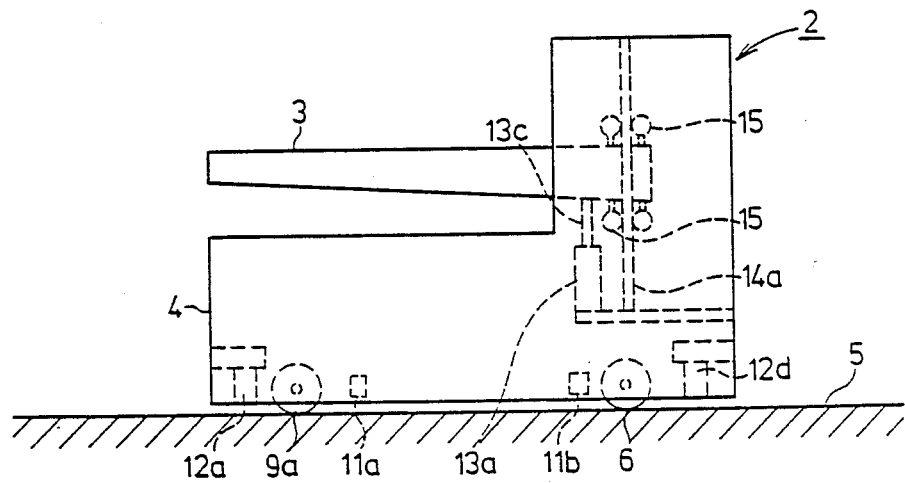

In FIGS. 2 and 3, "6" designates a driving wheel in contact with floor 5, which propels trolley 2. "7" designates a drive motor that drives driving wheel 6. 8 designates a steering device whose (right side) of the figure) is fixed to the wall of base 4. By extending or contracting the other end, the device can change the direction of driving wheel 6 centered at axis 6c. 37 9a and 9b" designate driven wheels with swivel bases fixed to base 4. "10" designates a guideline that sets the course of the moving trolley. This course is formed but not limited by using reflecting tape on floor 5. Such a guideline may be formed by using magnetism or radio waves, in which case a magnetic sensor or a radio wave detector is used. "11a and 11b" designate guideline sensors fixed to base 4. These are optical sensors that detect reflection from reflecting tape 10. Detection signals from guideline sensors 11a and 11b are conducted via a signal line (not shown) to steering device 8. "12a, 12b, 12c, and 12d" are outriggers or posts, one end of each being fixed to base 4 and the other end of each extending or contracting hydraulically to lock or unlock trolley section 2 against or away from floor 5.

"13a and 13b" are hydraulic cylinders in which pistons 13c and 13d move up and down. Other means, such as an electric motor, can be used to move the platform up and down. The lower ends of hydraulic cylinders 13a and 13b are fixed to base 4, while the upper ends of pistons 13c and 13d support the lower face of roof 3 and lift or lower the roof by their movement. "14a and 14b" are guide rails fixed to base 4 that guide the lifting or lowering movement of roof 4 while being sandwiched by camfollowers 15 fixed to roof 3. Eight cam-followers 15 are provided (two above, two below, two to the right, and two to the left of roof 3) toward the end closer to base 4 to sandwich guide rails 14a and 14b.

To apply a gantry of this invention in the operating room, guideline 10 must be formed in advance by using reflective tape between the operating table and a siding (not shown) for the gantry provided several meters away from the operating table. Guideline 10 may be formed without adversely affecting the floor face. The siding for the gantry is provided in a section that does not interfere with the operation. The gantry of this invention is to be delivered to the operating room and installed with the siding so that guideline sensors 11a and 11b are placed above guideline 10.

If tomography is required during surgery, the operator must press the forward switch (not illustrated) of trolley section 2 of the gantry in the siding. Then drive motor 7 drives driving wheel 6 to move trolley section 2 with gantry main body 1 forward to the operating table. During this movement, guideline sensors 11a and 11b detect the reflected light signal sent from guideline 10 formed on floor 5. Therefore, if trolley 2 goes off course, the volume of reflected light decreases. This actuates steering device 8 to turn the driving wheel 6 (centered on axis 6c) to correct the direction of trolley movement. Accordingly, trolley 2 moves correctly along guideline 10.

When gantry main body 1 is carried by the forward movement of trolley 2 to the required position near a patient on the operating table, the operator must press a stop button (not illustrated in the figure) to stop the forward trolley movement. Then, by using a roof up/-down switch (not illustrated), the level of roof 3 is adjusted to match the center of the section of the patient to be subjected to tomography with the center of the measuring space in gantry main body 1. In other words, when the roof up/down switch is pressed for upward movement, fluid is pumped into hydraulic cylinders 13a and 13b to move pistons 13c and 13d up to push roof 3 up. Then, cam-followers 15 attached to roof 3 smoothly lift roof 3 along guide rails 14a and 14b. When the roof up/down switch is pressed for down movement, the fluid inside hydraulic cylinders 13a and 13b is expelled to move pistons 13c and 13d down to lower roof 3. After determining the position of gantry main body 1, the gantry set switch (not illustrated) must be pressed by the operator to hydraulically lower outriggers 12a through 12d to floor 5 to fix trolley section 2 against the floor.

Tomography is subsequently done according to normal operation. If an other section of the patient's body is to be photographed, gantry main body 1 is set to the new position according to the same steps as described above after releasing the lock set by outriggers 12a through 12d. When tomography is completed, outriggers 12a through 12d are unlocked, and trolley section 2 returns to the siding as if the backward switch were pressed. When the backward switch is pressed, motor 7 revolves in the reverse direction to move trolley section 2 backward.

Guideline sensors 11a and 11b and steering device 8 control the course of movement in the same way as for forward movement.

As previously described, the gantry of this invention enables tomography according to simple operating steps at any time during an operation. Furthermore, the invention should not be limited to the specific details of examples of the previously described embodiments. For the illustrated preferred embodiments, trolley section 2 has one drive wheel and two driven wheels. Two drive wheels and one driven wheel may be alternatively used and two drive wheels may be driven independently and the trolley sections may be steered by controlling the number of revolutions of the left and right wheels. The number of outriggers or posts is not limited to four; some or all may can be eliminated if the floor is sufficiently level. While the previous examples show the use of hydraulic cylinders to lift or lower the roof, a motor cylinder consisting of a screw bar and nut may be alternatively used. Furthermore, for safety, the drive motor may be automatically braked at the time of power failure or a self-locking device with a gearbox may be alternatively used.

While the embodiments of this invention as herein disclosed constitute the preferred forms, other forms might be adopted with ease by those possessing knowledge in technological field to which this invention can be applied without departing from the spirit or claims as hereinunder stated.

We claim:

1. An apparatus for holding and roving a computerized tomograph gantry, said gantry comprising a generally circular hollow structure into which a body to be examined is received, said apparatus comprising a substantially horizontally disposed rectangular flat platform having a first end and opposite thereto a second end with a first linear dimension therebetween and perpendicular thereto a second linear dimension of said platform, said gantry being disposed on said platform at said first end thereof;

a base comprising a bottom, a first part, a second part, and a connecting part, said first part and said second part being connected to said connecting part with a horizontal space therebetween a linear dimension larger than said second linear dimension of said platform and extending from said connecting part of a linear dimension equal to the first linear dimension of said platform, said connecting part having a vertical dimension larger than a vertical dimension of said first and second parts;

means for vertically moving said platform between a position located between said first part and said second part of said base and a position located as high as the vertical dimension of the connecting part of said base, said means for vertically moving comprising a guide rail vertically extending and disposed within said connecting part of said base;

cam follower means connected to said platform at said second end thereof and disposed to contact said guide rail for holding said platform in substantially horizontal position while said platform is moved up and down;

power lifting means connected to said connecting part of said base and in contact with said platform toward said second end thereof, for lifting up and down said platform;

means for horizontally moving said base, said means for horizontally moving comprising at least one driven wheel movably connected to the bottom of said base;

means for steering said base while being horizontally moved, said means for steering comprising at least one steering wheel movably connected to the bottom of said base, means for causing said at least one steering wheel to turn in selected horizontal directions;

means for guiding the movement of said steering wheel in the selected horizontal directions, said means for guiding comprising guide means disposed on a floor below said bottom of said base, means for sensing the guide means and for sending signals indicative of the directions of said guide means to said means for causing the turning of the steering wheel; and motor means for driving said at lest one driven wheel and said at least one steering wheel.

2. The apparatus of claim 1, wherein said means for sensing comprises an optical sensor.

3. The apparatus of claim 1, wherein said means for sensing comprises a magnetic sensor.

4. The apparatus of claim 1, wherein said means for sensing comprises a radio wave detector.

5. The apparatus of claim 1, wherein further comprising a plurality of vertically extendible outriggers attached to the bottom of said base.

6. The apparatus of claim 1, wherein said power lifting means comprises a hydraulic cylinder.

7. The apparatus of claim 1, wherein said power lifting means comprises an electric motor.

8. An apparatus for holding and moving a computerized tomograph gantry, said gantry comprising a generally circular hollow structure into which a body to be examined is received, said apparatus comprising a horizontally disposed rectangular platform having a first end and a second end opposite thereto with a first linear dimension therebetween and perpendicular thereto a second linear dimension of said platform, said gantry being disposed on said platform at said first end thereof;

a base comprising a first part, a second part, and a connecting part, said first part and said second part being connected to said connecting part with a horizontal space therebetween of a linear dimension larger than said second linear dimension of said platform and extending from said connecting part of a linear dimension equal to the first linear dimension of said platform, said connecting part having a vertical dimension larger than a vertical dimension of said first and second parts;

means for movably holding said second end of said platform to said connecting part of said base;

means for vertically moving said platform to a position vertically located between a top of said first and second parts of said base and a position located vertically at a top of said connecting part of said base; and means for horizontally moving said base.

* * * * *